United States Patent [19]
Kampe et al.

[11] 3,931,214
[45] Jan. 6, 1976

[54] 2-AMINO-2-OXAZOLINES AND PROCESS FOR PREPARING THEM

[75] Inventors: Klaus-Dieter Kampe, Neuenhain, Taunus; Milos Babej, Frankfurt am Main; Joachim Kaiser, Bad Soden, Taunus, all of Germany

[73] Assignee: Hoechst Aktiengesellschaft, Frankfurt am Main, Germany

[22] Filed: Oct. 31, 1973

[21] Appl. No.: 411,240

[30] Foreign Application Priority Data
Nov. 2, 1972  Germany............................ 2253554

[52] U.S. Cl......... 260/307 F; 260/307 DB; 260/454; 260/553 R; 260/553 A; 424/272
[51] Int. Cl.$^2$..................................... C07D 263/28
[58] Field of Search ...................... 260/307 F, 307 D

[56] References Cited
UNITED STATES PATENTS
3,110,650  11/1963  Fischer et al. ........................ 167/65
3,124,589  3/1964  Poss et al............................. 260/307
3,161,650  12/1964  Poos .................................. 260/307

OTHER PUBLICATIONS

Carson et al. – J. Org. Chem. 30(7), 2225–2226 (1965).

Fishbein et al. – C.A. 51, 4283d (1957).

Takeda et al. – C.A. 14, 179$^4$ (1920).

Kanao et al. – C.A. 44, 1054f (1950).

*Primary Examiner*—Raymond V. Rush
*Attorney, Agent, or Firm*—Curtis, Morris & Safford

[57]  ABSTRACT

New 2-amino-2-oxazolines and their salts with physiologically tolerated acids which may be used as medicaments, in particular as antihypotonics, diuretics or antiphlogistics, and process for preparing them.

3 Claims, No Drawings

2-AMINO-2-OXAZOLINES AND PROCESS FOR PREPARING THEM

The present invention relates to 2-amino-2-oxazolines and to a process for preparing them.

The present invention provides 2-amino-2-oxazolines of the formula I

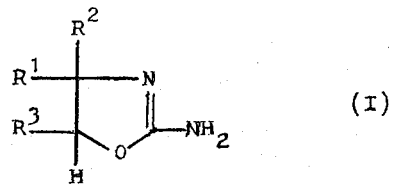

in which $R^1$ represents alkyl of 1 to 6 carbon atoms, vinyl, halogeno-alkyl or halogeno-alkenyl of 1 to 2 chlorine or bromine atoms and 1 to 4 or 2 to 4 carbon atoms, phenyl, phenyl which may be substituted by 1 or 2 methyl groups and/or alkoxy groups of 1 to 2 carbon atoms and/or by chlorine or bromine, cycloalkyl of 5 to 6 carbon atoms, carbomethoxy or carboethoxy, and $R^2$ and $R^3$ each represent hydrogen or alkyl of 1 to 3 carbon atoms, $R^1$ and $R^3$ together may further be members of a 5-, 7- or 8-membered carbocyclic ring or of a bi- or tricyclic carbocyclic ring system of 7 to 12 carbon atoms and if $R^1$ stands for a phenyl group $R^2$ is then a methyl group, and the salts of the compounds of the formula I with physiologically tolerated acids.

The radicals $R^1$ preferably represent alkyl of 1 to 4 carbon atoms, vinyl, chloromethyl, bromomethyl, dichloroethyl, dibromoethyl, chlorovinyl, bromovinyl, phenyl or carbomethoxy, $R^2$ and $R^3$ each represent hydrogen or methyl, or the radicals $R^1$ and $R^3$ together represent a trimethylene, pentamethylene or hexamethylene radical and $R^2$ represents hydrogen or methyl.

Furthermore, preferred 2-amino-2-oxazolines of the formula I are the compounds V to VII

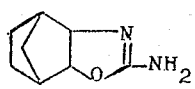

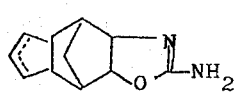

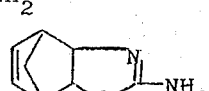

As physiologically tolerated acids, there are suitable, for example: hydrochloric acid, hydrobromic acid and hydriodic acid, sulfuric acid, phosphoric acid, toluenesulfonic acid, benzenesulfonic acid, sulfamic acid, fatty acids such as acetic acid, propionic acid, butyric acid, oleic acid, palmitic acid or stearic acid, furthermore oxalic acid, malonic acid, succinic acid or glutaric acid and malic acid, tartaric acid, citric acid, fumaric acid, maleic acid, lactic acid, glycolic acid, pyruvic acid, benzoic acid, salicylic acid or mandelic acid.

The present invention furthermore provides a process for preparing 2-amino-2-oxazolines of the formula II

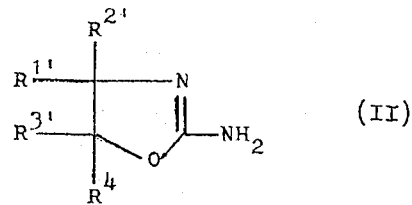

in which $R^{1'}$ represents alkyl of 1 to 6 carbon atoms, vinyl, halogenoalkyl or halogenoalkenyl of 1 to 2 chlorine or bromine atoms and 1 to 4 or 2 to 4 carbon atoms, phenyl, phenyl which may be substituted by 1 or 2 methyl groups and/or alkoxy groups of 1 to 2 carbon atoms and/or 1 chlorine or bromine atom, cycloalkyl of 5 to 6 carbon atoms, carbomethoxy or carboethoxy, $R^{2'}$ and $R^{3'}$ represent each, independently of each other, hydrogen or alkyl of 1 to 3 carbon atoms, $R^4$ represents hydrogen, methyl, ethyl, phenyl, halogenoalkyl of 1 to 2 carbon atoms and 1 chlorine, bromine or iodine atom, and $R^{1'}$ and $R^{3'}$ together may be members of a carbocyclic ring with 5, 6, 7 or 8 carbon atoms or of a bi- or tricyclic carbocyclic ring system of 5 to 12 carbon atoms, and their salts, preferably their physiologically tolerated salts.

According to the process a β-halogenoalkyl-isocyanate of the formula III

in which $R^{1'}$ to $R^{3'}$ and $R^4$ have the meanings given above and Hal represents chlorine or bromine, is reacted, optionally in the presence of an organic solvent which is miscible with water, with aqueous ammonia at a temperature of between 0° and 35° C, the β-halogenoalkyl-urea which has formed and corresponds to the formula IV

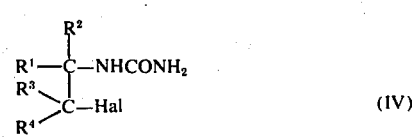

in which $R^{1'}$ to $R^{3'}$ and $R^4$ have the meaning given above. The β-halogenoalkyl-urea is isolated, treated with water at a temperature between 40° and 150° C, the hydrohalide which has formed during the reaction and corresponds to the formula IIa

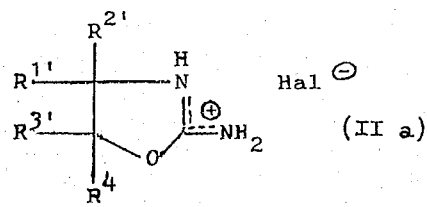

is converted at a temperature of between −5° C and +40° C suitably by the addition of an equivalent amount of alkali metal or alkaline earth metal hydroxide or carbonate into the 2-amino-2-oxazoline of the formula II

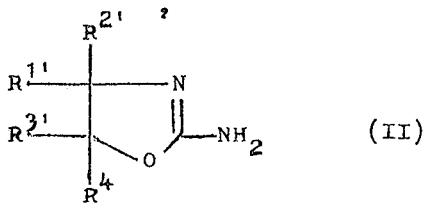
(II)

This product is isolated from the aqueous solution by extraction or crystallization and, if desired, subsequently converted into a salt by the addition of an acid.

$R^{1'}$ represents preferably alkyl of 1 to 4 carbon atoms, vinyl, chloromethyl, bromomethyl, dichloroethyl, dibromoethyl, chlorovinyl, bromovinyl, phenyl or carbomethoxy;

$R^{2'}$ and $R^{3'}$ represent each, independently of each other, hydrogen or methyl, $R^4$ represents hydrogen, methyl, phenyl, chloromethyl, bromomethyl or iodomethyl, or $R^{1'}$ and $R^{3'}$ together represent alkylene of 3 to 6 carbon atoms or one of the bi- and tricyclic systems of the compounds V to VII.

The process of the invention is preferably carried out with a β-chloroethyl-isocyanate or β-bromoalkyl-isocyanate; the reaction is effected with aqueous ammonia at a temperature of between 3° and 27° C and after following cyclization at 50° to 105° C, the 2-amino-2-oxazolines are set free from their hydrohalides with alkali at 0° to 25° C.

As basic compounds for setting free the amino-oxazolines of the formula II from their hydrohalides, sodium or potassium hydroxide or carbonate is preferably used.

As organic solvent which is miscible with water and is used in the reaction of a β-halogenoalkyl-isocyanate of the formula III with aqueous ammonia, there is suitable, for example tetrahydrofurane, 1,2-dimethoxyethane, dioxane, acetone, acetonitrile, dimethylformamide, dimethyl-sulfoxide, alkanols of 1 to 3 carbon atoms and/or glycol-methyl ether. In principle, the solvent is added in such an amount to the aqueous system that the β-halogenoalkyl-urea of the formula IV that has formed remains largely undissolved.

With tertiary isocyanates, the use of such a solvent is in general of advantage, with secondary or primary isocyanates, from a carbon number of 6 onwards in the isocyanate of the formula III, it is in general suitable in the reaction with the aqueous ammonia to use a solvent in a proportion of between 0.5 to 35 percent by volume, preferaby 1 to 23 percent by volume, referred to the volume of the reaction mixture.

The process of the invention may also be carried out without the organic solvent which is miscible with water.

In the reaction of the β-chloro- or β-bromoalkyl-isocyanate of the formula III with ammonia, there is formed the corresponding β-chloro- or -β-bromoalkyl-urea of the formula IV which separates from the ammoniacal aqueous solution largely in crystalline form or at first also in the form of a viscous oil. These ureas are isolated, for example by filtration or decantation, washed and then, after addition of the, suitably, 2 to 30-fold quantity by weight of water, heated for a period ranging from 3 minutes to 4 hours to a temperature in the range of from preferably 50° to 105° C. During that time the ureas of the formula IV pass into the hydrochloride or hydrobromides of the formula IIa which in general remain dissolved in the quantity of water used. The 2-amino-2-oxazolines of the formula II can be set free as strong bases from the hydrohalides of the formula IIa by the addition of strongly basic reagents and isolated. For converting the 2-amino-2-oxazolines into the corresponding salts, the 2-amino-2-oxazolines are reacted according to known methods with the respective acid.

The β-bromoalkyl-isocyanates required as preferred starting substances are easily accessible according to the process described in DOS No. 1,930,329 with a considerably width of variation regarding the substituents. In addition to β-chloroethyl-, β-chloroisopropyl- and β-chloro-tert.butyl-isocyanate, the following β-bromoalkyl-isocyanates may be used as starting substances according to the invention: β-bromoethyl-, β-bromopropyl-, β-bromoisopropyl-, bromo-tert.butyl-, β-bromo-sec.butyl-, 2,3-dibromopropyl-, 4,4,4-trichloro-2-bromo-butyl-, 1-bromomethyl-propyl-, 1-methyl-1-bromomethyl-butyl-, 1-bromomethyl-pentyl-, 1-vinyl-2-bromo-ethyl-, 1-methyl-1-vinyl-2-bromo-ethyl-, 1-phenyl-2-bromo-ethyl-, 1-phenyl-1-methyl-2-bromo-ethyl-, β-chloro-β'-bromo-tert.butyl-, 1-bromomethyl-2,3-dichloropropyl-, 1-bromomethyl-2-chloro-2-propenyl-, 1-bromomethyl-2-bromo-2-propenyl-, 1-bromomethyl-3-methyl-butyl-, 2-bromo-cyclopentyl-, 2-bromo-cyclohexyl-, 2-bromo-cycloheptyl-, 2-bromo-cyclooctyl- or 3-bromo-bicyclo[2,2,1]heptyl-2-isocyanate and 6(5)-bromo-5(6)-isocyanato-3a,4,5,6,7a-hexahydro-4,7-methano-indene.

It is known from Chem. Reviews 44, (1949) 447 to prepare 2-amino-2-oxazolines by cyclization of β-chloro- or β-iodo-alkyl-ureas in the presence of water at boiling temperature. Thereby, the hydrochlorides or -iodides of the amino-oxazolines are formed from which the free bases are obtained by the addition of alkalis or ammonia. The β-chloro- or β-iodo-alkyl-ureas were prepared from the corresponding β-chloro- or β-iodoalkyl-isocyanates by the action of gaseous ammonia in ether. However, since β-chloroalkyl-isocyanates must be prepared passing over several steps from 2-amino-alchohols, which themselves often are accessible with difficulty only, and since the preparation of corresponding β-iodoalkyl-isocyanates is very expensive and likewise gives unsatisfactory yields, only a few 2-amino-2-oxazolines have been synthetized in this way. Another process described in U.S. Pat. No. 3,629,276, on the other hand, starts from 2-amino-alcohols which are often accessible with difficulty only and are available only in the form of a few representatives and which are reacted with the extremely poisonous bromo-cyan under formation of 2-amino-2-oxazolines.

In contradistinction thereto, the process of the invention can be carried out very easily on an industrial scale and operates, contrary to the known methods, with harmless, easily accessible and, compared with the β-iodoalkyl-isocyanates, relatively cheap starting substances.

It must be considered surprising that the reaction of the isocyanates of the formula III with ammonia in the presence of an excess of water, which as is known likewise reacts easily with isocyanates, yields in a smooth reaction practically the pure ureas of the general formula IV. It is known that additions on isocyanates are carried out as far as possible in an inert solvent.

It is furthermore surprising that the β-chloro-, in particular the β-bromo-alkyl-ureas of the formula IV formed are stable under the conditions of the reaction of the isocyanates with aqueous ammonia, i.e. in the presence of water, and can subsequently be easily isolated in pure form.

The unexpected smooth course of the reaction of β-halogeno-alkyl-isocyanates of the formula III with aqueous ammonia permits the preparation of pure 2-amino-2-oxazolines according to the process of the invention which is superior to the known prepartion methods.

The new 2-amino-2-oxazolines of the formula I and their salts with physiologically tolerated acids may be used as medicaments. Among others, they have an action on the blood circulation, for example they cause a long-lasting increase of the blood pressure. Furthermore, they have a salidiuretic action, the ratio of the excreted ions $Na^+/K^+$ being especially favourable. In addition, an antiphlogistic action and an influence on the central nervous system was also observed. Therefore, the compounds of the invention may be used as antihypotensive agents, as diuretic and antiphlogistic agents, in admixture with the usual pharmaceutical excipients and adjuvants. As single doses, doses of 1 to 500 mg, preferably 10 to 250 mg, are used. These doses may be administered one to three times daily in the form of liquid preparations, for example in the form of drops, syrups or injection solutions, or in the form of solid preparations, for example as tablets, dragees, capsules or suppositories. The liquid preparations may also be administered as permanent infusions.

Particularly highly effective antihypotensive agents among the 2-amino-2-oxazolines are, for example 4,4-dimethyl-, 4-methyl-4-n-propyl-, 4,5-pentamethylene- and 4,5-hexamethylene-2-amino-2-oxazoline and cis-2-amino-3a,4,5,6,7,7a-hexahydro-4,7-methano -benzoxazole of the formula V (cf. page 3).

Particularly highly effective salidiuretic agents among the 2-amino-2-oxazolines are, for example 4-methyl-4-n-propyl-, 4,5-dimethyl-, cis-4,5-trimethylene- and 4,5-hexamethylene-2-amino-2-oxazoline.

Furthermore, the new 2-amino-2-oxazolines of the formula I may be used as intermediate products in the preparation of medicaments and plant protecting agents. Finally, the pure enantiomers of chiral 2-amino-2-oxazolines of the formula I as strong optically active bases may be used with advantage as reagents in the resolution of racemates.

The following Examples illustrate the invention:

EXAMPLE 1

33 g (0.2 mole) of β-bromoisopropyl-isocyanate were added dropwise, within 45 minutes, while cooling, at 4°–7° C, and stirring thoroughly, to a mixture of 50 ml of concentrated ammonia and 50 ml of ice-water. The whole was stirred for 5 minutes at 4°–7° C, the urea that had precipitated was filtered off with suction, washed with about 80 ml of ice-water and the urea was combined with 40 ml of water. This mixture was rapidly heated to 85° C, while stirring, and kept for 10 minutes at this temperature. After cooling, the aqueous solution was combined at 10°–15° C with 16.5 ml of 12 N-sodium hydroxide solution, saturated with NaCl and extracted several times with $CH_2Cl_2$. The combined extracts were dried over magnesium sulfate, filtered and evaporated at 37° C under reduced pressure. 15.5 g (77.5 percent of the theory) of racemic 2-amino-4-methyl-2-oxazoline were obtained in the form of a viscous colourless oil.

This oil was dissolved in 30 ml of ethanol and 20 ml of methanol and combined with a warm solution of 23.3 g L(+)-tartaric acid in 90 ml of ethanol. Upon cooling, 18.8 g (48.5 percent of the theory) of almost pure R-L(+)-2-amino-4-methyl-2-oxazoline-hydrogeno-tartrate crystallized ($[\alpha]_D^{25}$: + 27.6° ($H_2O$, C = 1.03); Mp. 151°–152° C). 1 g of this substance was then recrystallized from methanol and the resulting pure product showed the following data: Mp. 153°–154° C, $[\alpha]_D^{25}$: + 29.1° ($H_2O$, C = 1.012).

The hydrogeno-tartrate was dissolved in 30 ml of water and combined at 5°–10° C with 12.5 ml of 12 N-sodium hydroxide solution. The aqueous solution was extracted several times with $CH_2Cl_2$. The combined $CH_2Cl_2$ extracts were evaporated, after having been dried and filtered, and the residue was crystallized from isopropyl ether and hexane and once again recrystallized. 3.6 g (36 percent of the theory) of pure R(+)-2-amino-4-methyl-2-oxazoline were obtained; Mp. 66°–67° C, $[\alpha]_D^{25}$: 86.1° ($H_2O$, C = 1.01).

Analysis: $C_4H_8N_2O$: Calc.: C, 48.0 %, H, 8.0 %; N, 28.0 %; MW, 100.12. Found.: C, 48.1 %; H, 8.1 %; N, 27.8 %; MW, 100.

Upon addition of the equivalent amount of acetic acid to a solution of 10 g of R(+)-2-amino-4-methyl-2-oxazoline in 10 ml of isopropanol, the crystalline acetate precipitated immediately. After addition of 10 ml of ethyl acetate, the product was filtered off with suction, the crystalline acetate was recrystallized from a mixture of isopropanol and ether. 12 g (75 percent of the theory) of pure R(+)-2-amino-4-methyl-2-oxazoline were obtained; Mp. 118°–110° C, $[\alpha]_D^{25}$: +19.2° ($H_2O$, C = 1.01).

Analysis: $C_6H_{12}N_2O_3$: Calc.: C, 45.0 %; H, 7.5 %; N, 17.5 %; MW, 160.17. Found.: C, 45.0 %; H, 7.7 %; N, 17.5 %.

The mother liquor remaining after filtration with suction of the crystallized R-L(+)-hydrogen-tartrate (cf. above) was evaporated lunder reduced pressure. The remaining viscous vitreous residue (20 g) was dissolved in 30 ml of water and combined, while cooling, with 13.7 ml of 12 N-sodium hydroxide solution. The solution was saturated with sodium chloride and extracted several times with $CH_2Cl_2$. The combined extracts were worked up as described above. 9 g of oil were obtained which crystallized after addition of isopropyl ether and hexane. The isolated crystalline product was recrystallized twice from isopropyl ether and hexane. 2.55 g (25.5 percent of the theory, referred to the enantiomer) of pure S(-)-2-amino-4-methyl-2-oxazoline were obtained; Mp. 66°–67° C, $[\alpha]_D^{25}$: −85.9° ($H_2O$, C = 1.01).

EXAMPLE 2

33 g (0.2 mole) of R(-)-β-bromoisopropyl-isocyanate were reacted with aqueous ammonia as described in Example 1 and worked up in a manner analogous to said Example 1. 15.5 g of crude R(+)-2-amino-4-methyl-2-oxazoline (77.5 percent) were obtained. This product was crystallized with the aid of a mixture of isopropyl ether and hexane and recrystallized twice from this mixture. 10.8 g (54 percent of the theory) of pure R(+)-2-amino-4-methyl-2-oxazoline were obtained; Mp. 66°–67° C, $[\alpha]_D^{25}$: + 86.0° ($H_2O$, C = 1.01)

A part of this product was converted in an ethanolic solution with the equivalent amounts of L(+)-tartaric acid into the R-L(+)-tartrate which was recrystallized from methanol; Mp. 153°–154° C, $[\alpha]_D^{27}$: + 29.25° ($H_2O$, C = 1002).

EXAMPLE 3

17.8 g (0.1 mole) of β-bromo-sec.butyl-isocyanate were reacted with aqueous ammonia in the manner described in Example 1 and the isolated urea was further treated to obtain the amino-oxazoline. 11.0 g (96 percent of the theory) of crude base were obtained in the form of a viscous oil.

Preparation of the fumarate

The crude base (11.2 g) was dissolved in 10 ml of ethanol and combined with a hot solution of 10.8 g (0.093 mole) of fumaric acid in 200 ml of ethanol. Upon cooling, at first 4.5 g (26 percent of the theory) of neutral fumarate crystallized; Mp.: 202°–204° C.

Analysis: $C_{14}H_{24}N_4O_6$: Calc.: C, 48.8 %; H, 7.0 %; N, 16.3 %; MW, 344.36. Found.: C, 48.7 %; H, 7.1 %; N, 16.4 %.

The filtrate was concentrated to about half of its original quantity, whereupon 8.5 g (37 percent of the theory) of 2-amino-4,5-dimethyl-2-oxazoline-hydrogeno-fumarate (cis / trans mixture) crystallized; Mp. 146°–147° C.

Analysis: $C_9H_{14}N_2O_5$: Calc.: C, 46.9 %; H, 6.1 %; N, 12.2 %; MW, 230.22. Found.: C, 46.7 %; H, 6.1 %; N, 12.1 %.

EXAMPLE 4

Starting from 36 g (0.2 mole) of β-bromo-sec.butyl-isocyanate (threo-erythreo 1:1 mixture), there were obtained when working analogously to the method described in Example 1, after evaporation of the methylene chloride extract, 20.2 g (89 percent of the theory) of crystalline 2-amino-4,5-dimethyl-2-oxazoline (cis/trans mixture) as a residue. This product was recrystallized from 100 ml of isopropyl ether, whereby 13 g of crystalline product were obtained; Mp. 86°–88° C.

Analysis: $C_5H_{10}N_2O$: Calc.: C, 52.6 %; H, 8.8 %; N, 24.5 %; MW, 114.15. Found.: C, 52.3 %; H, 9.0 %; N, 24.3 %; MW, 114.

When the product was further recrystallized from isopropyl ether, there was obtained a product melting at 102°–104° C with a strong reduction of the quantity of crystalline material. This phenomenon is due to a fractionated crystallization of the cis/trans mixture which was modified in favour of one stereo-isomer.

Acetate formation 14.2 g of the 2-amino-4,5-dimethyl-2-oxazoline (Mp. 85°–87° C) prepared as described above were dissolved in 55 ml of ethyl acetate and combined with 7.45 g of glacial acetic acid, whereupon the acetate crystallized. After having added 8 ml of ether, the product was filtered off with suction. 20 g of acetate were isolated, which were recrystallized from 120 ml of ethyl acetate. Thereafter, 17.5 g (91 percent of the theory) of pure 1-amino-4,5-dimethyl-2-oxazoline-acetate (cis/trans mixture) were obtained; Mp. 108°–111° C.

Analysis: $C_7H_{14}N_2O_3$: Calc.: C, 48.3 %; H, 8.1 %; N, 16.1 %; MW, 174.20. Found.: C, 48.3 %; H, 8.2 %; N, 16.1 %.

EXAMPLE 5

35.3 g (0.2 mole) of 2-bromo-1-vinyl-ethyl-isocyanate were reacted in the manner described in Example 1 with aqueous ammonia. The corresponding isolated urea was combined with 40 ml of water and heated for 20 minutes to 75° C. The solution obtained was clarified with "Clarcel" filtering agents, filtered off with suction, combined at 5° C with 16.5 ml of 12 N-potassium lye and extracted several times with $CH_2Cl_2$. The combined dried $CH_2Cl_2$ extracts were evaporated under reduced pressure after having been filtered, whereupon 22.2 g of crystalline crude base remained behind. This product was recrystallized from 50 ml of isopropyl ether and 50 ml of hexane, which yielded 20.8 g (93 percent of the theory) of pure 2-amino-4-vinyl-2-oxazolone; Mp. 49°–50° C.

Analysis: $C_5H_8N_2O$ Calc.: C, 53.5 %; H, 7.2 %; N, 25.0 %; MW, 112.13. Found.: C, 53.4 %; H, 7.2 %; N, 25.0 %; MW, 112.

Fumarate formation

A solution of 14.8 g (0.132 mole) of 2-amino-4-vinyl-2-oxazoline in 10 ml of ethanol was combined with a hot solution of 15.5 g of fumaric acid in 160 ml of ethanol. Upon cooling, a crystalline precipitate separated. After having filtered off with suction, the filtrate was concentrated under reduced pressure to one third of its original volume, whereupon another crystalline substance precipitated. In this manner, 21.5 g (96 percent of the theory) of neutral 2-amino-4-vinyl-2-oxazoline-fumarate were obtained; Mp. 154°–155° C.

Analysis: $C_{14}H_{20}N_4O_6$: Calc.: C, 49.4 %; H, 5.9 %; N, 16.5 %; MW, 340.33. Found.: C, 49.7 %; H, 6.0 %; N, 16.3 %.

EXAMPLE 6

35.6 g (0.2 mole) of bromo-tert.butyl-isocyanate were added dropwise, within 1 hour, while stirring thoroughly, at 22°–25° C, to a mixture of 50 ml of concentrated aqueous ammonia, 40 ml of water and 15 ml of dioxane. The whole was stirred for 40 minutes at room temperature, the urea that had precipitated was filtered off with suction, washed well with water and combined with 50 ml of water. The mixture was heated for 20 minutes to 80° C, then cooled in an ice-bath and further worked up as described in Example 5. 21.8 g of crystalline crude base were obtained. This product was shortly boiled up under reflux with 250 ml of isopropyl ether. The warm isopropyl ether solution was decanted from a small amount of undissolved oil, concentrated under reduced pressure to about half of its original volume, whereupon the 2-amino-4,4,-dimethyl-2-oxazoline crystallized. After filtration with suction and after isolation of other crystallized material from the concentrated mother liquor, there wr were obtained 18.2 g (80 percent of the theory) of pure 2-amino-4,4,-dimethyl-2-oxazolone; Mp. 70°–71° C.

Analysis: $C_5H_{10}N_2O$: Calc.: C, 52.6 %; H, 8.8 %; N, 24.5 %; MW, 114.15. Found.: C, 52.3 %; H, 8.8 %; N, 24.7 %; MW, 114.

Acetate

The preparation was carried out analogously to the method described in Example 4. The acetate, which was obtained directly, was recrystallized from a mixture of ethyl acetate and isopropyl ether (5:1); Mp. 138°–139° C.

Analysis: $C_7H_{14}N_2O_3$: Calc.: C, 48.3 %; H, 8.1 %; N, 16.1 %; MW, 174.20. Found.: C, 48.5 %; H, 8.2 %; N, 16.3 %.

Fumarate

The preparation was carried out analogously to the method described in Example 3. 2-Amino-4,4-dimethyl-2.oxazoline-hydrogeno-fumarate; Mp. 191°–192° C.

Analysis: $C_9H_{14}N_2O_5$: Calc.: C, 46.9 %; H, 6.1 %; N, 12.2 %; MW 230.22. Found.: C, 47.1 %; H, 6.2 %; N, 12.1 %.

EXAMPLE 7

62 g (0.3 mole) of 1-methyl-1-bromomethyl-butyl-isocyanate were added dropwise, within 1 hour, while stirring, at room temperature to a mixture of 75 ml of concentrated aqueous ammonia, 60 ml of water and 40 ml of dioxane. Stirring was continued for 5 hours at room temperature. The oil that had separated was dissolved in methylene chloride and the aqueous solution was extracted several times with $CH_2Cl_2$. The combined, dried and filtered extracts were evaporated, whereupon 56 g of an oily substance were obtained which was combined with 100 ml of water and heated for 15 minutes, while stirring, to 85° C. After cooling, 30 ml of 10 N-sodium hydroxide solution were added at 5° C and the mixture was extracted several times with chloroform. After the usual working up of the combined extracts, 42 g of oily crude base were obtained. This product was converted into the fumarate. The 42 g of base were dissolved in 10 ml of ethanol and a hot solution of 32 g (0.276 mole) of fumaric acid in 320 ml of ethanol was added. The solution was concentrated to half of its original volume, whereupon a crystalline precipitated. After filtration with suction, the mother liquor was evaporated and the residue was recrystallized from a mixture of isopropanol and ether. In this manner 33.4 g (43 percent of the theory) of a 2-amino-4-methyl-4-n-propyl-2-oxazoline-hydrogeno-fumarate were obtained; Mp. 169°–170° C.

Analysis: $C_{11}H_{18}N_2O_5$: Calc.: C, 51.1 %; H, 7.0 %; N, 10.8 %; MW, 258.27. Found.: C, 51.1 %; H, 7.0 %; N, 11.0 %.

EXAMPLE 8

21 g (0.1 mole) of 1-methyl-1-bromomethyl-butyl-isocyanate were added dropwise, within 1 hour, at room temperature to a mixture of 25 ml of concentrated aqueous ammonia, 25 ml of water and 10 ml of isopropanol. Stirring was continued for 3½ hours and the reaction mixture was then extracted several times with methylene chloride. The whole was worked up as described in Example 7. 13.7 g of oily crude base were isolated from which 14.6 g (56.5 percent of theory) of hydrogeno-fumarate (cf. Example 7) were obtained; Mp. 169°–170° C.

EXAMPLE 9

19 g (0.1 mole) of 1-methyl-1-vinyl-2-bromoethyl-isocyanate were added dropwise within 1 hour, at 22°–24° C, to a mixture of 25 ml of concentrated ammonia and 25 ml of water. Stirring was continued for 30 minutes at room temperature. The corresponding urea precipitated in the form of a clotty crystal mass. This man was isolated, kneaded several times with water and worked up as described in Example 1. 9.8 g of oily crude base were obtained. This base was converted as described in Example 5 into a hydrogeno-fumarate. 12.6 g (52 percent of the theory) of 2-amino-4-methyl-4-vinyl-2-oxazoline-hydrogeno-fumarate were obtained; Mp. 183°–184° C.

Analysis: $C_{10}H_{14}N_2O_5$: Calc.: C, 49.6 %; H, 5.8 %; N, 11.6 %; MW 242.23. Found.: C, 49.6 %; H, 6.2 %; N, 11.7 %.

EXAMPLE 10

19 g (0.1 mole) of 1-methyl-1-vinyl-bromoethyl-isocyanate were added dropwise, within 1 hour, at room temperature, to a mixture of 25 ml of concentrated ammonia, 20 ml of water and 10 ml of tetrahydrofurane. Then, 5 ml of tetrahydrofurane were added, the whole was stirred for 45 minutes at 27° C and the urea was filtered off with suction and worked up as described in Example 1. 14.1 g (58 percent of the theory) of 2-amino-4-methyl-4-vinyl-2-oxazoline-hydrogeno-fumarate were obtained; Mp. 183°–184° C.

EXAMPLE 11

42.5 g (0.2 mole) of β-bromo-β'-chloro-tert-butyl-isocyanate were added dropwise, while stirring, at 20°–23° C, to a mixture of 50 ml of concentrated ammonia, 40 ml of water and 15 ml of dimethoxyethane. Stirring was continued for 1 hour at room temperature. The isolated urea was heated for 15 minutes to 80° C with 40 ml of water and worked up as described in Example 1. 22.4 g of crude base were obtained which was combined with 350 ml of isopropyl ether and then decanted from a layer of undissolved oil. The solution was evaporated and the residue was recrystallized from 50 ml of isopropyl ether. 8.4 g (28 percent of the theory) of 2-amino-4-methyl-4-chloromethyl-2-oxazoline were obtained; Mp. 61°–62° C.

Analysis: $C_5H_9ClN_2O$: Calc: C, 40.4 %; H, 6.1 %; Cl, 23.9 %; N, 18.8 %; MW, 148.59. Found.: C, 40.0 %; H, 6.1 %; Cl, 23.8 %; N, 18.4 %; MW, 148/150.

Fumarate

The 2-amino-4-methyl-4-chloromethyl-2-oxazoline was converted into the method described in Example 5 into a hydrogenofumarate; Mp. 182°–183° C.

Analysis: $C_9H_{13}ClN_2O_5$: C, 40.8 %; H, 4.9 %; Cl, 13.4 %; N, 10.6 %; MW, 264.67. C, 41.2 %; H, 5.2 %; Cl, 13.3 %; N, 10.4%.

EXAMPLE 12

38 g (0.2 mole) of trans-2-bromo-cyclopentyl-isocyanate were added dropwise, in 50 minutes, while stirring, at 12°–15° C, to a mixture of 60 ml of concentrated ammonia, 35 ml of water and 15 ml of dioxane. Stirring was continued for 40 minutes at 23° C. The corresponding isolated urea was heated for 30 minutes to 90°–93° C with 50 ml of water. Then, working up was carried out as described in Example 5. 18.3 g (73 percent of the theory) of crystalline crude base were obtained; the base was recrystallized from a mixture of ethyl acetate and isopropyl ether (1:2), and yielded 14.3 g (57 percent of the theory) of pure cis-2-amino-4,5-trimethylene-2-oxazoline; Mp. 110°–112° C.

Analysis: $C_6H_{10}N_2O$: Calc.: C, 57.1 %; H, 8.0 %; N, 22.2 %; MW, 126.16. Found.: C, 57.3 %; H, 8.0 %; N, 22.1 %; MW, 126.

EXAMPLE 13

19 g (0.1 mole) of trans-2-bromo-cyclopentyl-isocyanate were added dropwise, within 40 minutes, at room temperature, to a mixture of 30 ml of concentrated ammonia, 20 ml of water and 112 ml of acetone. The whole was stirred for 1 hour at this temperature and worked up as described in Example 12, but using instead of 12 N-potassium hydroxide solution 37 ml of 30 percent (by weight) of soda solution for setting free the base from the hydrobromide. 7.3 g (58 percent of the theory) of cis-2-amino-4,5-trimethylene-2-oxazoline were obtained; Mp. 109°–112° C.

EXAMPLE 14

20.5 g (0.1 mole) of cis/trans-(1:1)-2-bromocyclohexyl-isocyanate were added dropwise, within 50 minutes, at 8°–10° C, to a mixture of 25 ml of concentrated ammonia, 25 ml of ice-water and 7 ml of dioxane. Stirring was continued for 50 minutes at 8°–20° C and the urea was filtered off with suction. The urea was combined with 200 ml of water and the whole was heated for 25 minutes to 98° C. Upon cooling of the aqueous solution, a by-product (12 g) crystallized which had been formed from the cis-portion of the isocyanate. The whole was filtered with suction and the cold filtrate, which had been concentrated under reduced pressure to 70 ml and had been saturated with NaCl, was combined with 4.2 ml of 12 N-sodium hydroxide solution and extracted several times with $CH_2Cl_2$. The combined and dried filtrates were filtered and evaporated under reduced pressure. 5.3 g (76 percent of the theory) of oily crude base remained behind; the base was converted as described in Example 5 into the fumarate. 5.3 g (54 percent of the theory) of neutral cis-2-amino-4,5-tetramethylene-2-oxazoline-fumarate were obtained; Mp. 208°–210° C (literature: 210.5°–211.5° C).

Analysis: $C_{18}H_{28}N_4O_6$: Calc.: C, 54.5 %; H, 7.1 %; N, 14.1 %; MW, 396.44. Found.: C, 54.2 %; H, 7.3 %; N, 14.4 %.

EXAMPLE 15

21 g (0.1 mole) of 1-bromomethyl-3-methyl-butyl-isocyanate were added dropwise within 1 hour, at 8°–11° C, to a mixture of 25 ml of concentrated ammonia, 25 ml of water and 7 ml of 1,2-dimethoxyethane. Stirring was continued for 15 minutes at 12°–14° C, and then working up was carried out as described in Example 1. 11.6 g (82 percent of the theory) of oily 2-amino-4-isobutyl-2-oxazoline were obtained, which had been previously dissolved and reprecipitated from a mixture of isopropyl ether and hexane and finally evaporated in a high vacuum.

Analysis: $C_7H_{14}N_2O$: Calc.: C, 59.1 %; H, 9.9 %; N, 19.7 %; MW, 142.20. Found.: C, 58.8 %; H, 9.7 %; N, 19.9 %; MW, 142.

The 2-amino-4-isobutyl-2-oxazoline-hydrogeno-fumarate was prepared according to the method described in Example 5 and was found to melt at 102°–104° C, after recrystallization from isopropanol.

Analysis: $C_{11}H_{18}N_2O_5$: Calc.: C, 51.1 %; H, 7.0 %; N, 10.8 %; MW, 258.27. Found.: C, 51.3 %; H, 6.9 %; N, 10.6. %.

EXAMPLE 16

A solution of 32 g of bromine in 50 ml of $CH_2Cl_2$ was added dropwise, while stirring, at about 20° C, to a solution of 16.6 g (0.2 mole) of allyl-isocyanate in 100 ml of $CH_2Cl_2$. When the addition of bromine was completed, the methylene chloride was evaporated under reduced pressure at room temperature. The liquid residue was added dropwise, while stirring, within 1 hour, at 2°–4° C, to a mixture of 50 ml of concentrated ammonia, 50 ml of water and 8 ml of 1,2-dimethoxyethane. Stirring was continued for 10 minutes at 0°–2° C. The isolated urea was then worked up as described in Example 5. Upon addition of 12 N-potassium hydroxide solution to the aqueous solution of the 2-amino-5-bromomethyl-2-oxazoline-hydrobromide, the major part of the free base (26 g) precipitated immediately in crystalline form. The aqueous filtrate was extracted thrice with ethyl acetate. From these extracts, further 3.3 g of crystalline base were obtained after the usual working up. The crystalline crude base was recrystallized from acetone, whereupon 18.2 g (51 percent of the theory) of pure 2-amino-5-bromomethyl-2-oxazoline were obtained; MP. 120°–121° C (literature: 120° C; Monatshefte 5, 33 (1884); J. Chem. Soc. (London) 76, 16 (1899)).

EXAMPLE 17

About 14.5 g of chlorine were introduced within 50 minutes, at 20°–25° C, into a solution of 16.6 g (0.2 mole) of allyl-isocyanate in 100 ml of chloroform. The chloroform was subsequently evaporated under reduced pressure at a bath temperature of 30° C and the residue was reacted with aqueous ammonia in the manner described in Example 16 and under the conditions indicated in the said Example. Heating of the corresponding urea in water was extended to 35 minutes and the further working up was carried out in a manner analogous to that described in Example 16. When setting free the base from the corresponding hydrochloride, a part of the base separated immediately in crystalline form, the aqueous filtrate was likewise worked up as described in Example 16. From 22.4 g of crude base thus obtained, there were obtained, after recrystallization from a mxiture of acetone and ether, 16.9 g (63 percent of the theory) of pure 2-amino-5-chloromethyl-2-oxazoline were obtained; Mp. 142° C (literature: 142° C; Liebigs Annalen 442, 130 (1925).

EXAMPLE 18

70.5 g (0.3 mole) of cis/trans-(1:1)-2-bromo-cyclooctyl-isocyanate were added dropwise, within 50 minutes, at 8°–10° C, to a mixture of 75 ml of concentrated ammonia, 75 ml of water and 50 ml of dioxane. Stirring was continued for 40 minutes at 10°–24° C and the urea derivative was filtered off. By concentration under reduced pressure, a further quantity of urea derivative was obtained from the filtrate. The isolated N-(2-bromo-cyclohexyl)-urea was combined with 600 ml of water, heated to 93° C while stirring and combined with about 5 ml of 6N-sodium hydroxide solution (pH-value about 7). The whole was stirred for 20 minutes at 93° C; a clear solution formed with a small amount of a resinous precipitate. The solution was cooled to 3°–4° C after decanting. During that time an oily substance precipitated which was removed by filtration through silica gel. The filtrate was concentrated under reduced pressure to half of its original volume and combined with 45 ml of 6N-sodium hydroxide solution. The crystalline substance that had precipitated was dissolved in methylene chloride and the aqueous solution was extracted several times with methylene chloride. After drying over sodium sulfate and filtration, the combined methylene chloride extracts were evaporated under reduced pressure, whereupon 48 g of crude crystalline 2-amino-4,5-hexamethylene-2-oxazoline (cis/trans mixture) remained behind; Mp. 164°–167° C. From this mixture of the stereo-isomers, there were obtained by recrystallization from a mixture of acetone and isopropanol (7:1) (about 650 ml) 22 g of crystalline 2-amino-4,5-hexamethylene-2-oxazoline; Mp. 199°–201° C.

Analysis: $C_9H_{16}N_2O$: Calc.: C, 64.3 %; H, 9.6 %; N, 16.6 %; MW, 168.23. Found.: C, 64.5 %; H, 9.4 %; N, 16.3 %; MW, 168.

From the mother liquor, there were obtained by fractionated crystallization consecutively other fractions of crystalline 2-amino-4,5-hexamethylene-2-oxazoline with different melting points which were in the range of between 180° and 198° C. The analysis data of these crystal fractions corresponded well with those calculated for $C_9H_{16}N_2O$ (cf. above). From these crystal fraction, there could be obtained by repeated recrystallization from methanol, ethanol, isopropanol or ethyl acetate furtherequantities of the above-described 2-amino-4,5-hexamethylene-2-oxazoline; Mp. 199°–201° C.

2-Amino-4,5-hexamethylene-2-oxazoline- acetate

A solution of 13.45 g of 2-amino-4,5-hexamethylene-2-oxazoline (Mp. 199°–201° C) in 70 ml of ethanol was combined with 4.8 g of glacial acetic acid. After addition of 100 ml of ethyl acetate, 7.9 g of the formed acetate crystallized (Mp. 153°–155° C). After filtration, the filtrate was completely evaporated, the crystalline residue was combined with ether and filtered. In this manner, other 10.1 g of acetate were obtained.

Thus, the yield of 2-amino-4,5-hexamethylene-2-oxazoline-acetate was 18 g, corresponding to 99 percent of the theory; Mp. 153°–155° C.

Analysis: $C_{11}H_{20}N_2O_3$: Calc.: C, 57.9 %; H, 8.8 %; N, 12.3 %; MW, 228.29. Found.: C, 58.2 %; H, 8.9 %; N, 12.4 %.

In a manner analogous to that described in Example 18, there were prepared the following compounds:

from 2-bromo-cycloheptyl-isocyanate (cis/trans mixture or cis- or trans-form), the 2-amino-4,5-pentamethylene-2-oxazoline; Mp. 155°–157° C.

from 3-bromo-bicyclo[2.2.1]-heptyl-2-isocyanate (cis/trans mixture or trans-form), the cis-2-amino-3*a*.4.5.6.7.7*a*-hexahydro-4,7-methano-benzoxazole (compound V).

from 6(5)-bromo-5(6)-isocyanato-3*a*.4.5.6.7.7*a*-hexahydro-4.7-methano-indene (cis/trans mixture or trans-form), the cis-2-amino-3*a*.4.5.6.7.7*a*-hexahydro-4.7-methano-5,6-propeno-benzoxazole (compound VII).

We claim:
1. 4,4-Dimethyl-2-amino-2-oxazoline.
2. 4-Methyl-4-n-propyl-2-amino-2-oxazoline.
3. 2-Amino-3*a*.4.5.6.7.7*a*-hexahydro-4,7-methano-benzoxazole.

* * * * *